United States Patent [19]
Steinel

[11] Patent Number: 5,926,614
[45] Date of Patent: Jul. 20, 1999

[54] ELECTRIC DEVICE FOR THE VAPORIZATION OF ADDITIVES

[75] Inventor: Heinrich Wolfgang Steinel, Bad Wörishofen, Germany

[73] Assignee: Steinel Gmbh & Co. Kg, Herzebrock-Clarholz, Germany

[21] Appl. No.: 08/776,306

[22] PCT Filed: Jul. 24, 1995

[86] PCT No.: PCT/EP95/02917

§ 371 Date: May 28, 1997

§ 102(e) Date: May 28, 1997

[87] PCT Pub. No.: WO96/04021

PCT Pub. Date: Feb. 15, 1996

[30] Foreign Application Priority Data

Aug. 3, 1994 [DE] Germany ............................. 94112152

[51] Int. Cl.[6] ........................... A61M 16/00; H01R 39/00
[52] U.S. Cl. ............................................. 392/392; 439/13
[58] Field of Search ..................................... 392/392, 394, 392/395; 219/541; 439/13, 372, 373; 338/22 R, 23

[56] References Cited

U.S. PATENT DOCUMENTS

| | | | |
|---|---|---|---|
| 1,994,932 | 3/1935 | Vidal | 392/395 |
| 2,611,068 | 9/1952 | Wellens | 392/392 |
| 2,942,090 | 6/1960 | Diehl | 392/392 |
| 4,682,830 | 7/1987 | Nagashima . | |
| 4,874,924 | 10/1989 | Yamamoto et al. | 392/395 |
| 5,038,394 | 8/1991 | Hasegawa et al. | 392/395 |
| 5,222,186 | 6/1993 | Schimanski et al. | 392/395 |
| 5,352,122 | 10/1994 | Speyer et al. | 439/13 |

FOREIGN PATENT DOCUMENTS

| | | |
|---|---|---|
| 0 290159 | 11/1988 | European Pat. Off. . |
| 0 362397 | 4/1990 | European Pat. Off. . |
| 91 04 709 | 7/1991 | Germany . |
| WO 88/05310 | 7/1988 | WIPO . |

*Primary Examiner*—Teresa Walberg
*Assistant Examiner*—Sam Paik
*Attorney, Agent, or Firm*—Darby & Darby

[57] ABSTRACT

An electric device for the vaporization of additives has a housing in which an electric heating unit is disposed and into which the additive is to be inserted. The device has a heat exchanger, which is in heat connection with the heating unit and which is disposed at a location to vaporize the additive. The device includes a plug for a wall socket which is rotatable relative to the housing and has a rotating joint carrying a set of contacts. A set of counter-contacts is at the housing and arranged in a manner to produce an electric connection in two positions of the plug offset from the housing by about 90°, and an annular range in between having a switching position in which the connection is opened.

9 Claims, 5 Drawing Sheets

ELECTRIC DEVICE FOR THE VAPORIZATION OF ADDITIVES

The present invention refers to an electric device for the vaporization of additives according to the preamble of claim 1.

Devices of that kind have become more popular, e.g. for vaporizing scents and fragrances, to repel small insects, such as mosquitoes for example. These devices are preferably provided with a plug integrated within the housing, so that the device can be directly plugged into a socket.

A problem is that the device can normally only be operated in a certain position, since the additive is usually bound in a liquid carrier material or in a paste, and that leaking of the carrier material is only prevented in a certain position of the device, but the bushes of a wall socket can be on a horizontal or a ve rtical line.

There are devices existing which solve this problem by providing a plug within this housing which can be turned at an angle of approximately 90°. Then it is possible to pivot the housing of the device to the desired operating position.

Devices of that kind are known, which are provided with an electric switch, by means of which the heating can be turned on and off. The device does not have to be pulled out of the wall to be turned off.

The object of the invention is to provide a device of the above-mentioned kind, which is provided with an adaptor to vertical or horizontal wall sockets, and which is still of a simple design.

This object is solved on the basis of a device of the kind of the invention in that the plug is provided with a first rotating joint member, which is engages a second rotating joint member arranged within the housing and that contacts are arranged in each of the rotating joint members, which can be brought into and out of contact with the contacts associated to each of the respective contacts of the other rotating joint member.

The contacts and the respective counter-contacts on the two rotating joint members are arranged so that a continuous electrical connection between the plug contacts and the heating results in two positions offset by 90° and an angular range with a switch position results in which the connection is opened.

By providing the contacts and the respective counter-contacts on the two rotating joint member, a simplified construction of the device results which is turned on and off by rotating the housing with respect to the plug. The device can always take a certain turn-on position because the device has two turn-on positions offset by 90°, said operating position being independent from the fact whether the device is plugged into a vertical or a horizontal wall socket.

Moreover, an operator will easily recognize from the position of the housing in which operating condition the device is, since the housing is in a different position in the turned-off position than in the turned-on position of the device.

Preferably, the angular range with the closed connection is considerably smaller than the annular range with a closed connection, the ratio of the angular range with a closed connection to the angular range with an opened connection is 1:5.

In an advantageous embodiment, the heating comprises at least one PTC resistor, disposed between two metallic electrodes, connected to the contacts of the rotating joint member through electric connection conduits. PTC heating resistors are known to stabilize themselves at a temperature depending on their dimensions.

The construction of the device becomes much more easy if the connecting conduits, the contacts, the heat exchanger and possibly the electrodes are integrally formed of a punching sheet, which is bent after punching, if necessary and which is coated by a plastic material at the points at which an increased inhere nt stability or heat insula tion is required. The device becomes much more simple by providing the essential electrically conducting parts on a simple punching sheet, since otherwise the common strand connec- tion s become useless. Moreover, the electrically conducting parts get a higher strength due to the plastic material, which elongates the life of the device and reduces the electrical power loss.

In a preferred embodiment, the electric connecting con- duits are provided in the region between the contacts of the rotating joint member close to the housing in the form of two quarters of a ring di sposed on t op of each other, and the connecting conduits are bent at a position between the quarters of a ring and the electrodes about an angle of approximately 90° with respect to the electrodes. Preferably, the quarters of a ring are coated by plastic material in a manner that an almost closed ring results.

In this embodiment, the rotating joint member, close to the housing, is, after bending, vertical to the plane in which the electrodes and the heat exchanger are formed. This considerably simplifies the manufacturing process, since all manufacturing steps can be performed in one level and afterwards only a bending of the connecting conduits is necessary to bring the rotating joint member near the hous- ing to the required vertical position in which it is inserted into the housing.

The rotating joint member is preferably connected in a rigid connection to the plug, and is rotatably guided in the wall of the housing preferably about an angle of 90°. This design ensures that the operator can only turn the device between the two turn-on positions offset about 90°.

In a further advantageous further development, the rotat- ing joint members engage each other by means of a lock-in connection, which guarantees defined switching conditions of the device. The contacts of the one rotating joint member contacts in the turn-on position the counter-contacts of the other rotating joint member and a tight contact of the contacts is supported by the lock-in connection The present invention will new be explained under reference to the drawings.

Figure 1:
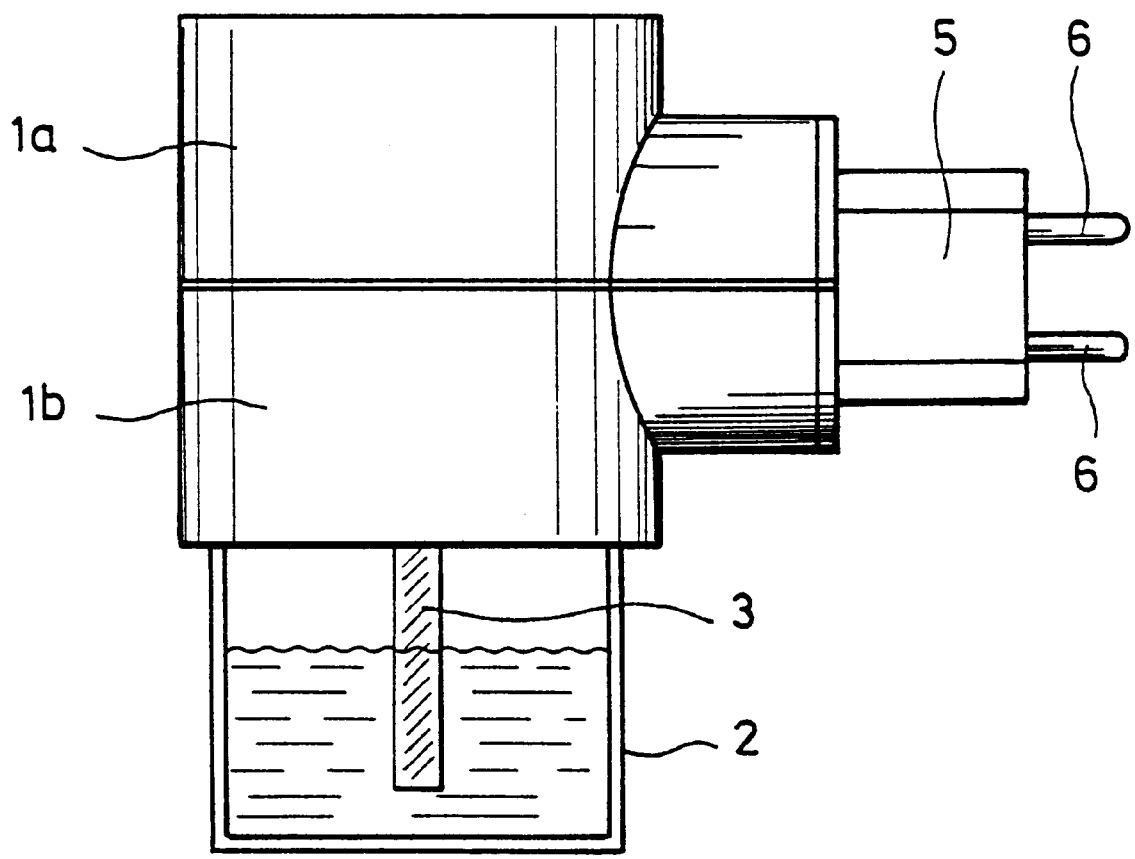
FIG. 1 is a lateral view of the device.

According to FIG. 1, the device comprises a housing consisting of two semimonocoque parts of the housing 1a, 1b, with a container 2 connectable thereto, in which the substance to be vaporized is located; e.g. a liquid with additives resolved therein. The attachment means between the housing and the container 2 consist of an external thread attached at the upper end of the container and a respective internal thread formed in the lower semimonocoque part of the housing 1b. A wick 3 is disposed within the container 2, consisting of carbon fibers or textile threads. The liquid to be vaporized is transported through the wick to the heating 4, closer defined in FIGS. 2 and 3. A plug 5 with two plug contacts 6 attached thereto is rotatably supported within the housing. As can be derived from FIG. 4, the plug comprises an annular groove 7, which engages a correspondingly formed edge of the semimonocoque parts of the housings 1a, 1b, if the housing is closed.

Figure 2:
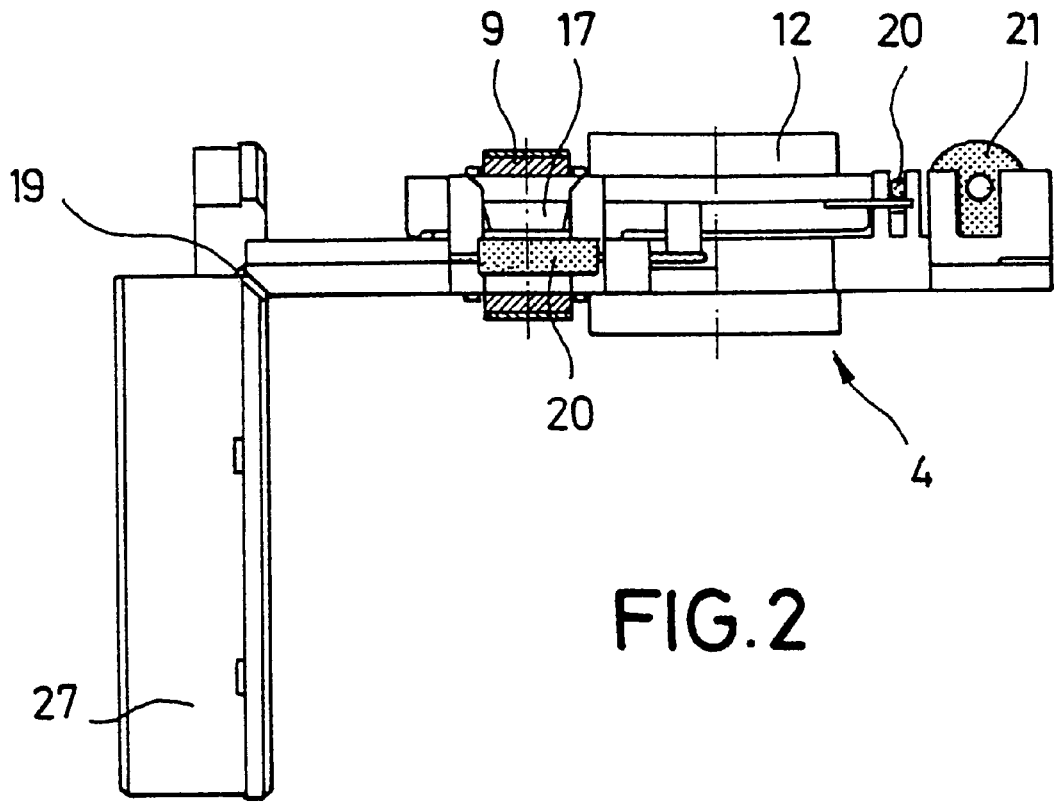
FIG. 2 is a lateral view of the heating of the device disposed within the housing.
Figure 3:
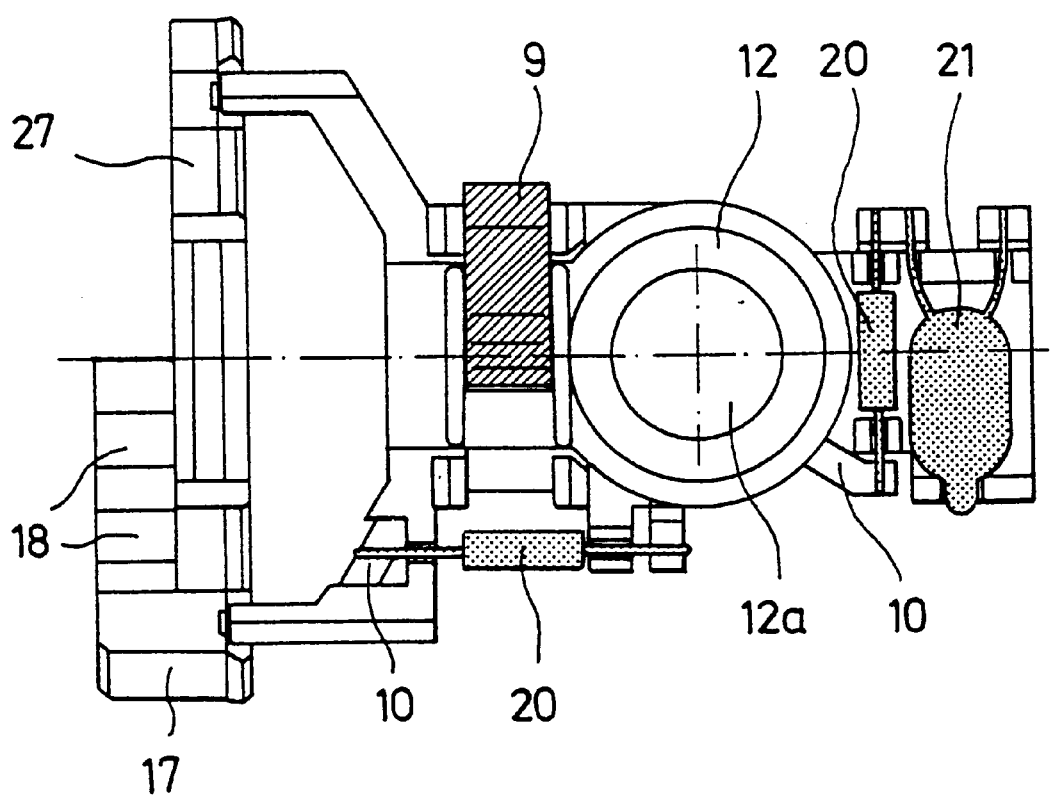
FIG. 3 is a top view of the heating, shown in FIG. 2.

The heating 4 comprises a PTC heating element clamped between two electrodes 8 disposed on top of each other, not directly shown in FIGS. 2 and 3, since the most part of the electrodes is coated by a heat resistant and insulating plastic material and prevents a free sight to the PTC element. The electrodes are embedded in the plastic material on the opposite side. The sides facing each other comprise a contact surface, which is large enough to completely contact the PTC element. A continuous web is formed along the outer edge of the electrodes, wherein the webs are disposed on the upper and lower electrode in a manner that they mesh with one another. Thereby, a closed cavity is formed, with which the PTC element is retained in form-fit fashion. A resilient, conductive element is disposed between the lower electrode an the PTC element, which, together with a U-shaped clamping spring 9 surrounding the electrodes from the outside, is responsible for a good contact between the electrodes and the PTC element. The electric part of the heating furthermore comprises connecting conduits 10, a part of which being connected through a region 11 having a reduced wire cross section to the electrodes 8, as can be seen more clearly in FIG. 6.

Figure 7:
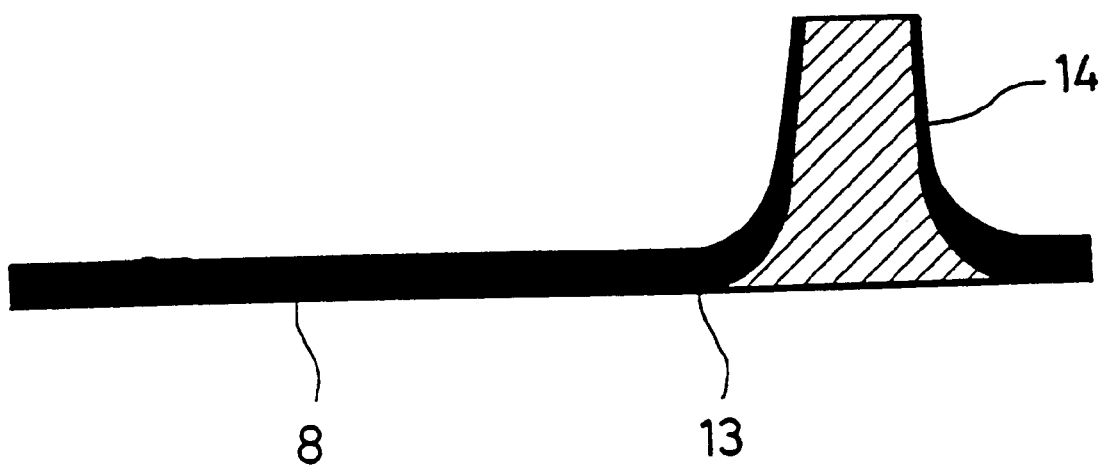
FIG. 7 is a magnified section of an electrode with a heat exchanger formed integrally therewith.

A heat exchanger 12 consists of two annular sections 13 disposed on top of one another, which comprise a molded setion 14 made of the same metallic material as the electrodes. As can be seen in FIG. 7, the ratio between the length of the molded region 13 to the thickness of the electrode is approximately 6:1. The molding process is performed in a manner that the material strength of the molded region diminishes towards the free end thereof. It is in particular important in molding that sufficient material is existing at the point between the molded section 14 and the annular section 13 so that a good heat transition is ensured on the molded part. The greater material thickness at the points, which are close to the heating element, leads to the result that the heating energy is transmitted well up to the outer ends. The annular and molded region 13 or 14 is completely embedded in the plastic material. The coated, annular and molded regions of the heat exchanger can be seen in FIG. 3, said heat exchanger comprising an axially centered passage channel 12a. The annular region is coated with a thin insulation material at the inner wall thereof, so that as much heat energy as possible c a n be conducted into the passage channel 12a. The outer wall of the annular region in turn, has a thick insulating layer, which becomes thicker towards the free end in the axial direction of the molded region. An insulation formed in that manner reduces the heat losses and is responsible that the heat transmitted in this manner is transported exactly to the desired point in the passage channel.

The essential steps of manufacturing a device according to the present invention will now be explained.

Figure 6:
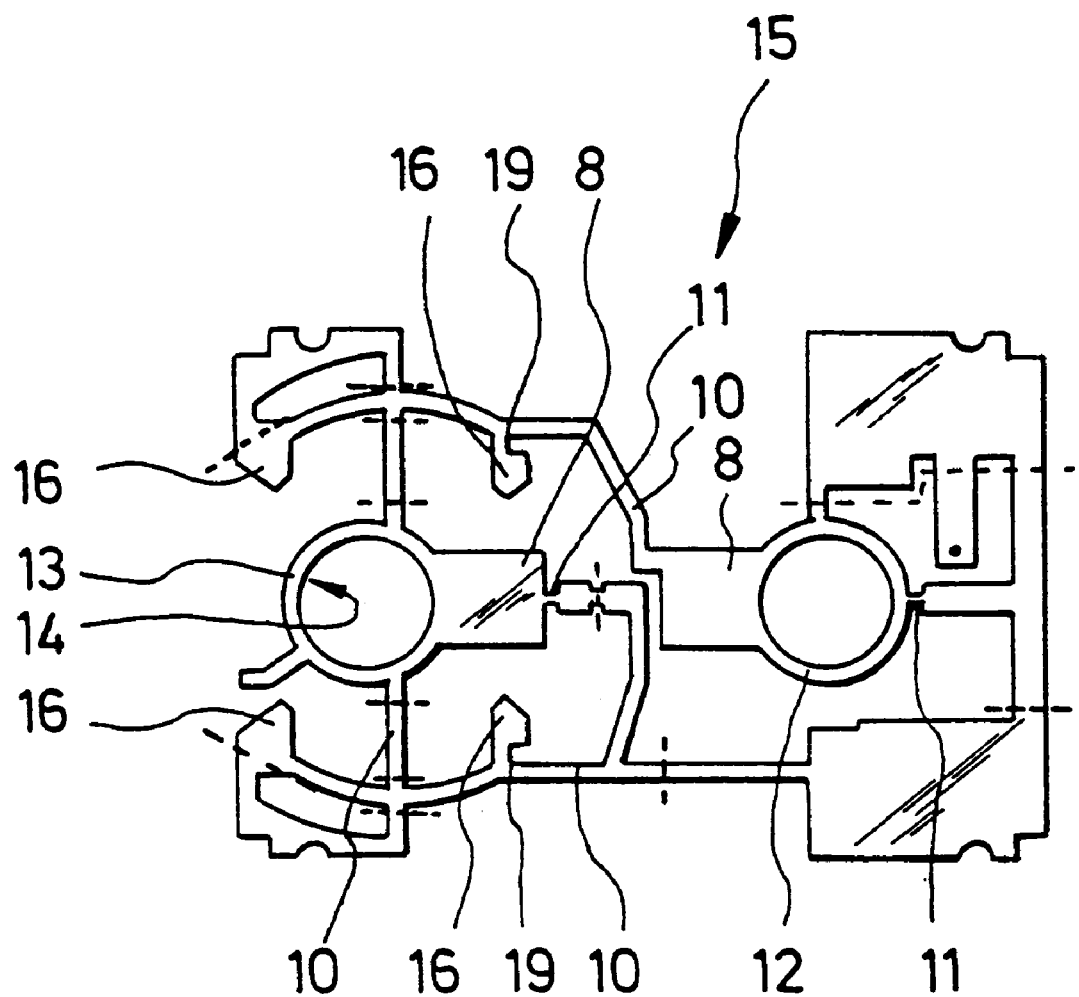
FIG. 6 is a view of the punching sheet member, contain- ing essential parts of the device.

FIG. 6 shows a punching sheet part 15 with the essential parts of the electric heating. In the completely punched condition, the sheet portions, shown in dotted lines in the drawing, are completely separated. Two electrodes 8 can be seen, with annular portions 13, formed integrally with the electrodes, each comprising a molded section 14. Connecting conduits 10 are integrally formed with the electrodes 8 and the annular section 13, partially via regions 11 having a reduced cross section. The connecting conduits are provided in the left half of the punching member, shown in FIG. 6, having the shape of a quarter of a circle and facing each other, and each of them carry a pair of contacts offset about 90°.

In a further method step, the punching sheet member is coated by a plastic material at the points at which an increased inherent stability or heat insulation is required. The coating of the rings having the shape of a quarter of a circle is carried out so that an almost closed ring is formed, with the contacts 16 projecting radially inwardly at the inner wall thereof. A web 17 is formed at the front side of the ring, said web extending in the axial direction of the ring. The web extends at a length of approximately a fourth of the ring and comprises a plurality of recesses 18 with bevelled surfaces (FIG. 3) at its inner wall. After the coating process, the spots shown with dotted lines in FIG. 6 are separated, which causes the electrode, shown in the left half, to completely fall out. Then, the connecting conduits, having the shape of a quarter of a circle, embedded into the almost closed ring, are bent at the portions 19 about 90° with respect to the remaining electric part of the heating, which can be seen in FIG. 2.

Finally, the heating is totally provided with resistors 20 and a light emitting diode 21.

During operation of the device, the electric circuit of the heating functions as follows: Starting at a connecting conduit 10, the heating current flows through safety resistor 20 to the upper annular section 13, integrally formed with the upper electrode 8. From this electrode, the current flows through the PTC heating element to the lower electrode 8 and then to a second connecting conduit 10, which is completely coated by a plastic material. The two connecting conduits 10 are connected with the plug contacts 6 of the plug 5, shown in FIG. 1. A protective resistor 20 is connected in parallel to the pair of electrodes 8, with a light emitting diode 21 connected in series thereto. The connecting conduits for the protective resistor and the light emitting diode are located at the upper and the lower annular section 13 of the heat exchanger 12.

PTC heating elements are known to stabilize themselves at a temperature depending on their dimensions. For the present embodiment, the PTC heating element was chosen so that it generates a temperature of 150° C. at the predefined operating voltage. Since the upper and the lower electrode 8 are in tight contact with the heating element, and the annular sections are integrally formed with the molded portion at the heating element, the heat generated by the heating element is transported to the heat exchanger 12. Based on the embodiment of the device according to the invention, the heat loss is so low that a temperature of approximately 128° C. is measured in the passage channel at the wick. The small temperature loss of only 22° C. with respect to the operating temperature of the PTC is remarkable. Furthermore a very small fluctuation of temperature of only 0.5° C. has been proven during long-time tests.

It has to be pointed to the fact, that the heating, which was described in the embodiment, is only an example and that a lot more of technical possibilities exist for realizing this heating. The heating element, for example, does not necessarily have to consist of a PTC heating element, but can also be a heating winding made of a heating wire, which is embedded in a ceramic heating body.

A different embodiment of the present invention, not shown in the drawings, differs from the above-mentioned embodiment by a different heat exchanger 8. In this embodiment, the annular section 13 and the molded section 14 are replaced by a planar heating surface. Furthermore, a container is provided which is located above the heating surface, e.g. a heat resistant plastic bowl, instead of the container 2 with the wick retained therein. The substance to be evaporated is situated in the bowl, which is regularly heated by the heating surface disposed directly underneath the bowl. In this embodiment the housing comprises a suitable opening, through which the container can be supplied with the substance to be evaporated.

Figure 4:
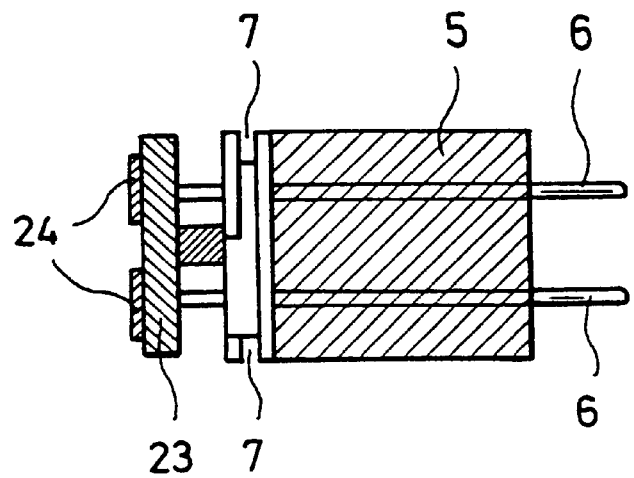
FIG. 4 is a lateral view to the plug and the first rotating joint member of the present invention.
Figure 5:
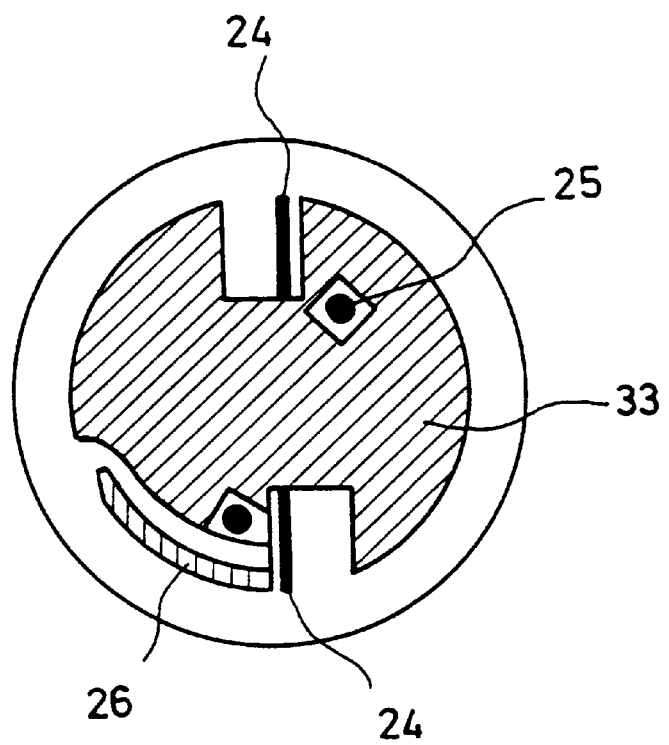
FIG. 5 is s front view of the first rotating joint member.

It will new be referred to FIGS. 4 and 5, which describe a first rotating joint member 22:

The first rotating joint member 22 is rigidly connected to the plug 5 and basically consists of a disk-like carrier portion 23, carrying two opposing strip-like electric contacts 24. The electric contacts 24 are connected to the plug contacts 6 through contact pins 25 (FIG. 5). A cam 26 is provided at the outer periphery of the disk-like carrier portion 23, said cam having two surfaces at its free end, including an angle of approximately 120° with one another.

A second rotating joint member 27 basically consists of the almost closed ring, which evolved from the coating of the connecting conduits 10, formed as a quarter of a circle (compare FIGS. 2 and 3) and of the web 17, connected thereto, which comprises a number of recesses.

If the device according to the invention is installed, the carrier portion 23 of the first rotating joint member 22 engages the annular second rotating joint member 27. The cam 26 formed at the carrier portion 23 engages into the recesses 18, formed at the inner wall of the second rotating joint member. If the plug 5 is rotated with the first rotating joint member attached thereto with respect to the housing, the cam 26 latchingly slides over the recesses 18 of the second rotating joint member. The rotation of the plug 5 with respect to the housing is limited by means of a limiting means, which is not shown in detail, to approximately 90°.

I claim:

1. A device for the vaporization of a volatile additive substance comprising:

a housing;

an electric heating device in said housing;

a heat exchanger in contact with said heating device disposed at a position relative to the additive to evaporate the additive;

a plug having plug contacts for a wall socket connected to said housing and having a rotating joint member rotatable relative to said housing carrying strip-like electric contacts electrically connected to said plug contacts;

counter contacts disposed within the housing opposing said rotatable strip-like electric contacts and electrically connected to said electric heating device, said strip-like electric contacts and said counter-contacts respectively arranged to come into contact to effect electrical connection between said plug contacts and said heating device in two positions of said plug relative to said housing offset by about 90°, and an angular range between said two positions in which there is no contact and the electrical connection is opened.

2. A device according to claim 1, wherein the angular range of a closed electrical connection is smaller than the angular range with an opened connection.

3. A device according to claim 2, wherein the ratio of the angular range with a closed connection to the angular range with an opened connection is less than 1:5.

4. A device according to claim 1 wherein said heating device comprises at least one PTC resistor, which is disposed between two metallic electrodes, which are connected through electric connecting lines to said counter-contacts near the housing.

5. A device according to claim 1, wherein said rotating joint member comprises a rigid connection with said plug and is rotatably guided in the wall of said housing.

6. A device according to claim 5, wherein said rotating joint member is rotatably guided in the wall of the housing at a 90° angle.

7. A device comprising:

a housing;

an electric heating device in said housing;

a heat exchanger in contact with said heating device disdosed at a position relative to the additive to evaporate the additive;

a plug having plug contacts for a wall socket connected to said housing and having a rotating joint member rotatable relative to said housing carrying electric contacts electrically connected to said plug contacts;

counter-contracts disposed within the housing opposing said electric contacts and electrically connected to said electric heating device, said electric contacts and said counter-contacts respectively arranged to come into contact to effect electrical connection between said plug contacts and said heating device in two positions of said plug relative to said housing offset by about 90°, and an angular range between said two positions in which the electrical connection is opened;

wherein said heating device comprises at least one PTC resistor, which is disposed between two metallic electrodes which are connected through electric connecting lines to said counter-contacts near the housing;

wherein said connecting lines, said counter-contacts, said heat exchanger and possibly said electrodes are integrally stamped from a sheet and coated by a plastic material at at least one selected point to provide an increased inherent stability or heat insulation.

8. A device according to claim 7, wherein said electric connecting lines are provided between the contacts of the rotating joint member close to the housing comprise two opposing quarters of a ring, and said lines have a part that are bent about an angle of approximately 90° with respect to said electrodes at a position between the quarters of a ring and said parts are coated by plastic material to form an almost closed ring.

9. A device comprising:

a housing;

an electric heating device in said housing;

a heat exchanger in contact with said heating device disposed at a position relative to the additive to evaporate the additive;

a plug having plug contacts for a wall socket connected to said housing and having a rotating joint member rotatable relative to said housing carrying electric contacts electrically connected to said plug contacts which rotate with said rotating joint member;

counter-contracts disposed within the housing opposing said electric contacts and electrically connected to said electric heating device, said electric contacts and said counter-contacts respectively arranged to effect electrical connection between said plug contacts and said heating device in two positions of said plug relative to said housing offset by about 90°, and an angular range between said two positions in which the electrical connection is opened;

wherein said contacts of said rotating joint member engages said counter-contacts through a lock-in connection.

* * * * *